US010434039B2

(12) United States Patent
Forsgren Brusk et al.

(10) Patent No.: US 10,434,039 B2
(45) Date of Patent: Oct. 8, 2019

(54) HYGIENE TISSUE

(71) Applicant: SCA Hygiene Products AB, Göteborg (SE)

(72) Inventors: Ulla Forsgren Brusk, Pixbo (SE); Bo Runeman, Partille (SE); Eva Gran Håkansson, Umeå (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 1433 days.

(21) Appl. No.: 14/225,929

(22) Filed: Mar. 26, 2014

(65) Prior Publication Data

US 2014/0205651 A1     Jul. 24, 2014

Related U.S. Application Data

(63) Continuation of application No. 10/318,165, filed on Dec. 13, 2002, now abandoned.

(60) Provisional application No. 60/339,386, filed on Dec. 13, 2001.

(51) Int. Cl.

| A61K 8/99 | (2017.01) |
| A61K 9/70 | (2006.01) |
| A61K 8/02 | (2006.01) |
| A61K 8/92 | (2006.01) |
| A61K 9/00 | (2006.01) |
| A61Q 19/00 | (2006.01) |
| A61Q 19/10 | (2006.01) |

(52) U.S. Cl.
CPC ............ *A61K 8/0208* (2013.01); *A61K 8/922* (2013.01); *A61K 8/99* (2013.01); *A61K 9/0014* (2013.01); *A61Q 19/00* (2013.01); *A61Q 19/10* (2013.01); *A61K 9/0034* (2013.01); *A61K 9/70* (2013.01)

(58) Field of Classification Search
CPC ...... A61K 8/0208; A61K 9/0014; A61K 8/99; A61K 8/922; A61K 9/70; A61K 9/0034; A61Q 19/10; A61Q 19/00
See application file for complete search history.

(56) References Cited

U.S. PATENT DOCUMENTS

| 4,518,696 A | 5/1985 | Gehrman et al. |
| 4,904,485 A | 2/1990 | Hirakawa et al. |
| 5,639,659 A | 6/1997 | Barefoot et al. |
| 5,645,830 A | 7/1997 | Reid et al. |
| 5,705,160 A | 1/1998 | Bruce et al. |
| 6,107,537 A | 8/2000 | Elder et al. |
| 6,365,656 B1 | 4/2002 | Green et al. |
| 6,716,435 B1 | 4/2004 | Farmer et al. |

FOREIGN PATENT DOCUMENTS

| EP | 1 118 342 | 7/2001 |
| WO | WO 92/13577 | 8/1992 |
| WO | WO 97/02846 | 1/1997 |
| WO | WO 97/29762 | 8/1997 |
| WO | WO 98/47374 | 10/1998 |
| WO | WO 99/17813 | 4/1999 |
| WO | WO 99/45099 | 9/1999 |
| WO | WO 00/35502 | 6/2000 |
| WO | WO 00/41576 | 7/2000 |
| WO | WO 00/76878 | 12/2000 |
| WO | WO 01/13956 | 3/2001 |

OTHER PUBLICATIONS

Hill, G.B. et al., Scand. J. Urol. Nephrol. 1984; 86 (suppl.) 23-29.
Runeman, B. et al., Acta Derm Venereol 2000; 80: 421-424.
Ap K adé va, B.A. et al., N A. Nauchnye Doklady Vysshei Shkoly, Biologicheskie Nauki, 1983, 2: 101-104.
Stoianova et al., Mikrobiologiia, 2000, 69: 98-104 (English abstract).
Harry's Cosmeticology 8th ed., Ed by MM Rieger, Chemical Publishing Co., Inc., New York, 2000.

*Primary Examiner* — Gollamudi S Kishore
(74) *Attorney, Agent, or Firm* — Buchanan Ingersoll & Rooney P.C.

(57) ABSTRACT

A hygiene tissue includes a composition including one or more lactic acid producing bacterial strains and a lipid phase including at least one lipid, wherein the lipid is selected from the group having olive oil, canola oil, coconut oil, palm kernel oil, peanut oil, soy bean oil, Dimethicone, paraffin oil, and petrolatum; and a matrix impregnated by the composition.

17 Claims, 19 Drawing Sheets

HYGIENE TISSUE

CROSS REFERENCE TO RELATED APPLICATIONS

This application is a continuation of U.S. Ser. No. 10/318,165, filed on Dec. 13, 2002, which claims priority under 35 U.S.C. 119(e) to U.S. Provisional Application No. 60/339,386 entitled PRODUCT and filed on Dec. 13, 2001, the entire content of which is hereby incorporated by reference.

BACKGROUND

1. Field of the Invention

The present invention relates to hygiene tissues to be used to establish and maintain a beneficial microbial flora on the skin and the urogenital area in combination with cleaning and caring of these areas.

2. Background of the Invention

The urogenital area harbors a complex microbial ecosystem comprising more than 50 different bacterial species (Hill et al., Scand. J. Urol. Nephrol. 1984; 86 (suppl.) 23-29). The dominating species in this area are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms, and competing for available nutrients, thereby excluding colonization by harmful microorganisms. Also, the production of enzymes, such as hydrogen peroxidase, and specific inhibiting substances, such as toxins and bacteriocines, and organic acids (including lactic acid and acetic acid) that lower the pH, inhibit colonization by other microorganisms. However, the microbial ecosystem of a healthy individual can be disturbed by the use of antibiotics, in people suffering from diabetes, during hormonal changes, such as during pregnancy or use of contraceptives with estrogen, during menstruation, after menopause, etc. Also, microorganisms can spread from the anus to the urogenital area, thereby causing infections. This results in a disturbance of the normal microbial flora and leaves the individual susceptible to microbial infections that cause vaginitis, urinary tract infections and ordinary skin infections. Microorganisms commonly associated with these kind of infections belong to the genera *Escherichia, Enterococcus, Psedomonas, Proteus, Klebsiella, Streptococcus, Staphylococcus, Gardnerella* and *Candida*. Women are at particular risk due to their shorter distance between the anus and the urogenital tract; specially at risk are young women, who not yet have a well developed microflora in the urogenital area and older women, who no longer have a protective flora.

Similarly to the urogenital area, the skin is colonized by an array of organisms, which forms its normal flora. The numbers and identity of the organisms vary between different skin sites. This, together with the skin's structural barrier, provides the host with an excellent defense against invading microbes. The number of bacteria on the skin vary from a few hundred per $cm^2$ on the arid surfaces of the forearm and back, to tens of thousands per $cm^2$ on the moist areas such as the axilla and groin. This normal flora plays an important role in preventing 'foreign' organisms from colonizing the skin, but it to needs to be kept in check, in order to avoid skin infections.

*Staphylococcus aureus* is a common cause of minor skin infections, such as boils or abscesses, as well as more serious post-operative wound infection. Treatment involves drainage and this is usually sufficient for minor lesions, but antibiotics may be given in addition when the infection is severe and the patient has fever. Toxic shock syndrome is a systemic infection caused by *S. aureus* strains which produce toxic shock syndrome toxin. The disease came to prominence through its association with tampon use by healthy women, but it is not confined to women and can occur as a result of *S. aureus* infection at non-genital sites.

Other common skin infections are caused by *Streptococcus pyogenes* (group A streptococci). The organisms are acquired through contact with other people with infected skin lesions and may first colonize and multiply on normal skin prior to invasion through minor breaks of the epithelium and the development of lesions. Treatment with penicillin or erythromycin may be necessary to combat the infection.

*Propionibacterium acnes* are found on normal human skin. The organism is no longer believed to be the cause of acne, but have been assigned a role in inflammation of acne.

*Malassezia* (formerly *Pityrosporum*) are probably universal inhabitants of the head and thorax in adult humans. Species of this organism are known to be involved in the skin diseases seborrhoeic dermatitis and pityriasis versicolor and to play a part in the aetiology of severe dandruff. These yeasts may also play a part in exacerbation of atopic dermatitis.

So called ringworm infections of the skin may be caused by dermatophyte fungi, e.g., *Tricophyton, Epidermophyton* and *Microsporum*.

The relative dryness of most areas of skin limits the growth of *Candida*, which therefore are found in low numbers on healthy skin. However *Candida* rapidly colonizes damaged skin and intertriginous sites (apposed skin sites which are moist and become chafed). *Candida* also colonizes the oral and vaginal mucosa and overgrowth may result in disease in these sites (so called thrush). *C. albicans* is associated with diaper dermatitis. A study has shown that *C. albicans* induced lesions are remarkably influenced by pH, a lower skin pH giving less lesions (B. Runeman, Acta Derm. Venereol. 2000; 80: 421-424).

One way to reduce the problems with the kind of infections described above is to have a good personal hygiene. However, excessive use of cleaning agents not only decrease the amount of harmful microbes, but can harm the beneficial microbial flora, again render it susceptible for pathogenic species to colonize and cause infections. Alternatively, administration of lactic acid producing bacteria to the urogenital area and the skin in order to out compete pathogenic species and facilitating establishment and maintenance of a beneficial microbial flora in these areas, have been found to be a successful means to treat and prevent microbial infections.

It has been suggested that lactic acid producing bacteria can be delivered via absorbent articles, such as diapers, sanitary napkins, panty liners and tampons, as described in, for example, in WO97/02846, WO99/17813, WO99/45099 and WO00/35502. However, absorbent articles may not always be an optimal administration route, since carrying of an absorbent article often is apprehended as uncomfortable, indiscrete and warm. This administration route can also be inconvenient as repeated administration of lactic acid producing bacteria often is necessary to retain the efficacy of the treatment or the preventative effect. Also, these products are not generally used for delivery of the bacteria to other regions of the body than the urogenital area. Therefore, for some applications it can be more convenient to administer lactic acid producing bacteria by other means than absorbent products. A second problem with administration of lactic acid producing bacteria via absorbent articles relates to the manufacturing of such products, since a wide selection of variants and sizes of the product have to be supplied with the bacteria. Therefore the administration via a product that could be used without individual adjustments could provide a manufacturing advantage over the absorbent products.

However, a problem with providing articles intended to be used for transfer of lactic acid producing bacteria, is that the bacteria have to retain viability during transport and storage of the articles. Lactic acid producing bacteria rapidly lose viability under moist conditions, and it is therefore important that the products are not exposed to moisture-. One way to partly overcome this problem has been to supply articles with freeze-dried lactic acid producing bacteria, thereby providing long shelf-life products containing viable lactic acid producing bacteria. However, the bacteria still have to be protected against moisture during the time between manufacturing and use.

Alternatively, research experiments have shown that storage in sterile vaseline oil results in a high level of viable lactobacilli cells after 8 months of storage, although survival of the bacterial cells is not discussed in the context of transferring bacteria to the skin (Arkadva et al., N A. Nauchnye Doklady Vysshei Shkoly. Biologicheskie Nauki, 1983, 2:101-104). In contrast, Stoianova et al. (Mikrobiologiia, 2000, 69:98-104) found that immersion in mineral oil was not effective to preserve viability of lactic acid producing bacteria. There are additional examples of the combination lactic acid producing bacteria and a fatty composition, although these do not describe the effect of the fatty composition on the survival pharmaceutical compositions comprising Emu oil, antimicrobial agents and/or *Bacillus coagulans* to be used for antimicrobial treatments. However, the object of using compositions described in WO01/13956 is to treat microbial infections by adding components that kill undesirable microorganisms and the Emu oil is not added to enhance survival of bacteria included in the compositions. WO92/13577 relates to a tampon or sanitary napkin that is coated with a compound with adhesive properties and subsequently added bacteria that attach to the adhesive compound. WO92/13577 neither relates to hygiene tissues nor mentions anything about a composition containing bacteria suspended in a lipid phase. U.S. Pat. No. 4,518,696 describes the stabilization of suspensions comprising lactobacilli by dispersing the bacteria in sunflower oil. However, this patent relates to the field of providing preparations of lactobacilli for oral administration to animals.

OBJECTS AND SUMMARY

There is still a need to develop products for delivery of lactic acid producing bacteria to the skin and urogenital area that are convenient to use, result in efficient transfer of the bacteria to the area where they are applied and can be stored for long time periods without loss of viability of the bacterial cells.

An object of the present invention is to provide a convenient device for the delivery of lactic acid producing bacteria to the skin and urogenital area. This is obtained by providing a hygiene tissue, comprising viable lactic acid producing bacteria, that can be used for cleaning and caring the skin while simultaneously delivering the lactic acid producing bacteria, to establish and maintain a beneficial microflora on the skin and the urogenital area. In order to provide products that can be stored for long time periods, without loss of viability of the lactic acid producing bacteria, the bacterial cells are suspended in a lipid that protects the bacteria from moisture. Also an object of the present invention is to provide moisture impervious packing units comprising the hygiene tissue of the invention.

One preferred embodiment of the present invention pertains to a hygiene tissue to be used for cleaning and caring of the skin and the urogenital area simultaneously as it delivers lactic acid producing bacteria, thereby establishing and maintaining a healthy microbial flora in these areas. The hygiene tissue is impregnated with a composition comprising a lactic acid producing bacterium/bacteria suspended in a lipid and optionally additional components. The present inventors surprisingly found that encapsulating the lactic acid bacterium in a lipid provided a moisturefree environment keeping the bacterium in a shape that resulted in enhanced longevity, high transfer rates to the skin, and still keeping fitness for survival and growth on the skin. Therefore, by this approach, bacterial survival was enhanced during long term storage. Also, the hygiene tissue of the preferred embodiment improved the efficiency of transfer of the lactic acid producing bacterium to the skin and urogenital area, simultaneously as the lipid served as a cleaning agent with skin caring properties. Furthermore, the embodiment relates to an impervious packing unit comprising the hygiene tissue described above.

BRIEF DESCRIPTION OF THE FIGURES

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS

Figure 1:
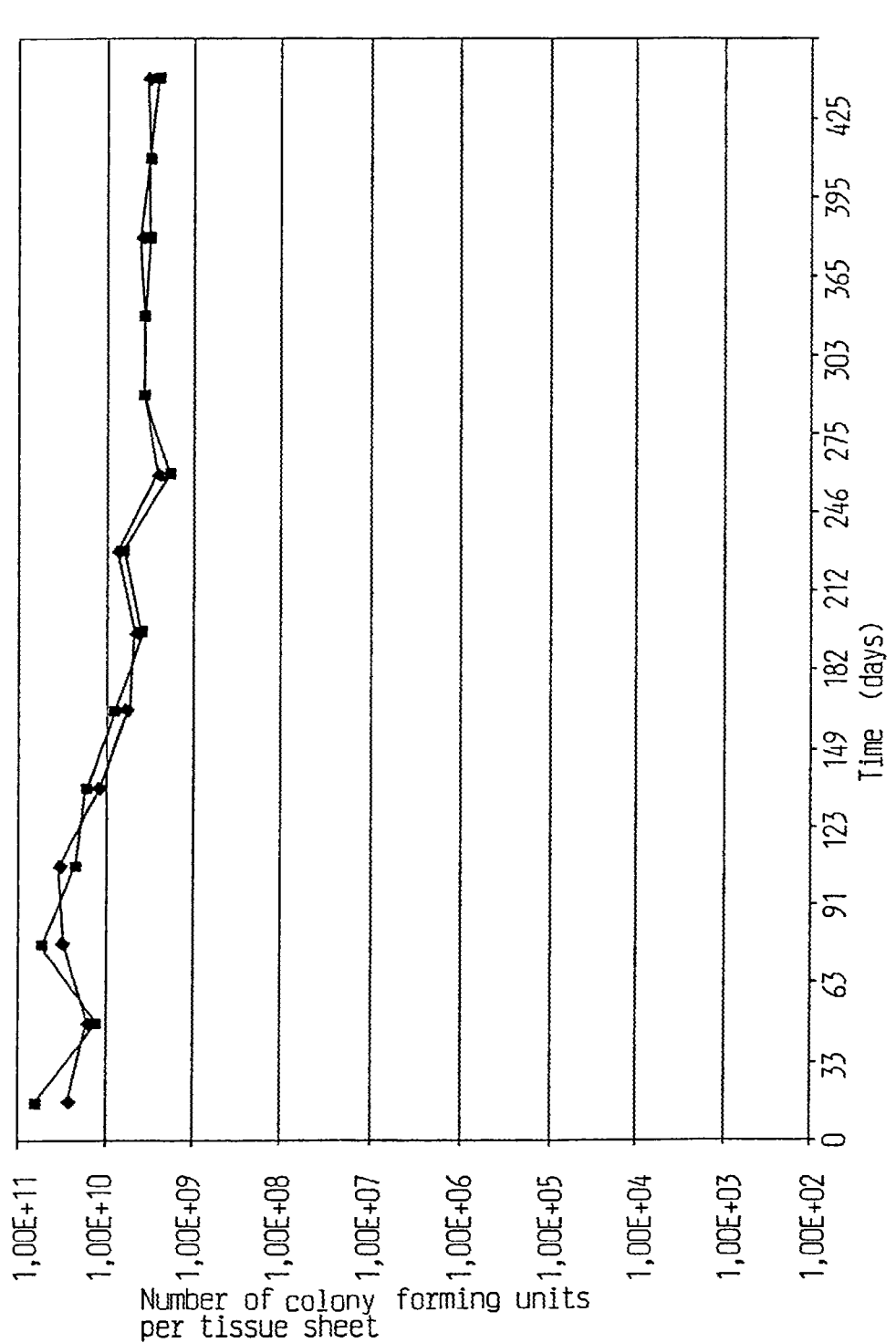
FIG. 1 shows the survival of *Lactobacillus plantarum* 931 in olive oil on hygiene tissues Spun Lace Dupont (.diamond-solid.) and SCA Absbond (.box-solid.).

By "hygiene tissue" is meant any device for wiping skin, for instance, a washcloth, patch, towelette, napkin, wetwipe, and the like.

By "matrix" is meant any natural or synthetic fiber, such as felt, batting, rayon, cellulose, regenerated cellulose, polyester, polyolefin fibers, textile and the like, or foam, or combinations thereof.

Preferred "lactic acid producing bacterium" include bacteria from the genera *Lactobacillus, Lactococcus* and *Pediococcus*. Preferably the selected bacterium used is from the species *Lactococcus lactis, Lactobacillus acidophilus, Lactobacillus* curvatus or *Lactobacillus plantarum*. Even more preferably the lactic acid producing bacterium is *Lactobacillus plantarum* 931 (deposition No. DSM: 11918).

By "lipid" is meant a water-insoluble organic molecule with a fatty character. Suitable lipids for the present invention include petroleum-derived lipids, synthetic lipids, and animal- and plant-derived lipids.

By "additional component" is meant agents commonly added to skin caring products, such as caring agents, water absorbent agents, pH buffering agents (weak organic or inorganic acids, such as lactic acid, ascorbic acid, citric acid or boric acid), perfume, antioxidants, hydrocortisone, other anti-inflammatory steroids, etc. Further details on suitable agents commonly added to skin caring products are given in Harry's Cosmeticology 8th ed., Ed by M M Rieger, Chemical Publishing Co., Inc., New York, 2000.

By "moisture impervious packing unit" is meant a packing unit having a highest water vapor transmission rate of 6 g/m.sup.2/calendar day in accordance with ASTME 398-83.

The hygiene tissue can be used for cleaning and simultaneously establishing and maintaining a healthy microbial flora on the skin and in the urogenital area. The hygiene tissue provided can be composed of a matrix comprising any natural or synthetic fiber, such as felt, batting, rayon, cellulose, regenerated cellulose, polyester, polyolefin fibers, textile and the like, or foam, or combinations thereof. The water content of the matrix of the hygiene tissue is preferably 10% or less (by weight), more preferably 5% or less (by weight), and most preferably 1% or less (by weight). The hygiene tissue is impregnated with a suspension of a lactic acid producing bacterium in a lipid. The lipid encapsulates the bacteria and thereby acts to protect the bacteria from moisture, which enhances bacterial survival during manufacturing and storage. Preferably the lactic acid producing bacteria are present directly in the lipid phase, but the bacteria can also be present in microincapsulated forms. Exposure to moisture during manufacturing and storage of products that comprise lactic acid producing bacteria, causes reactivation of the bacteria, which subsequently leads to their death. Therefore, by protecting the bacteria from moisture, their survival is enhanced and the durability of the product extended. The inventors also found that encapsulating the bacteria in lipid resulted in enhanced transfer rates to and survival of the bacteria on the skin after their delivery to it (see Example 3 below). This can be an effect of the lipid creating a micromilieu, that is beneficial for retaining bacterial viability and that enhances growth of the added bacteria on the skin. Also, the lipid has more adhesive properties than, for example, water, thereby resulting in a higher amount of bacteria actually being transferred to the skin. In addition to its bacterial survival enhancing properties, the lipid also serves as a skin treatment agent that cleans the skin without causing drying out. Once the bacteria have been delivered to the skin, the moisture on the skin reactivates the bacteria, thereby allowing them to perform their intended action, i.e., competitively exclude and minimize colonization of pathogenic microbial species. Optionally, additional substances, including water absorbent agents (such as inorganic salts, e.g., calcium chloride), tensides (non-ionic, amphoteric and anionic surfactants), pH buffering agents (weak organic or inorganic acids, such as lactic acid, ascorbic acid, citric acid or boric acid), perfume, antioxidants, hydrocortisone and other anti-inflammatory steroids, can also be added to the lipid-bacterial suspension, or directly to the hygiene tissue.

The amount of lipid suspension of lactic acid producing bacteria on the tissue is preferably 0.5-95% by weight.

The number of probiotic bacteria on the hygiene tissue is preferably $10^4$-$10^{11}$ colony forming units (CFU) and more preferably $10^6$-$10^{11}$ CFU. The preparation of lactic acid producing bacteria are preferably in a dried form, preferably as a freeze-dried powder. The bacteria can also be provided in microencapsulated forms. Preferably, the water activity of the bacterial preparation is about 0.30 or less, more preferably about 0.25 or less, and most preferably about 0.20 or less.

In one preferred embodiment the probiotic bacterial strain with antagonistic effect is selected from the genera *Pediococcus, Lactobacillus* or *Lactococcus* including combinations thereof. The lactic acid producing bacterial strain is preferably isolated from the skin or urogenital area of a healthy person.

In another preferred embodiment the probiotic bacterial strain with antagonistic effect is at least a *Lactobacillus plantarum* strain.

In an even more preferred embodiment the probiotic bacterial strain with antagonistic effect is at least *Lactobacillus plantarum* 931 (deposition No. (DSM): 11918).

Preferable lipids for the present invention support survival of the stored cells so that the maximum decrease in number of culturable cells is 3 log units after 12 months storage. Preferable lipids have a water content of 5% or less (by weight), preferably 3% or less (by weight), most preferably 1% or less (by weight). More preferably, suitable lipids support survival of the stored cells so that the maximum decrease in number of culturable cells is 2 log units after 12 months storage. Most preferably, suitable lipids support survival of the stored cells so that the maximum decrease in number of culturable cells is 1 log unit after 12 months storage.

Preferable lipids enable transfer of bacteria to the skin of 10.sup.5 or more culturable cells per cm.sup.2. More preferably, suitable lipids enable transfer of bacteria to the skin of 10.sup.6 or more culturable cells per cm.sup.2. Most preferably, suitable lipids enable transfer of bacteria to the skin of 10.sup.7 or more culturable cells per cm.sup.2.

Preferable lipids are also characterized by supporting survival of the bacterial cells on the skin so that 10.sup.2 or more culturable cells per cm.sup.2 can be recovered 12 hours after delivery by use of the hygiene tissue. More preferably, suitable lipids support survival of the bacterial cells on the skin so that 10.sup.3 or more culturable cells per cm.sup.2 can be recovered 12 hours after delivery by use of the hygiene tissue. Most preferably, suitable lipids support survival of the bacterial cells on the skin so that 10.sup.4 or more culturable cells per cm.sup.2 can be recovered 12 hours after delivery by use of the hygiene tissue.

Preferable lipids for the present invention include petroleum-derived lipids, such as paraffinum liquidum (mineral oils, paraffin oils, and vaseline oils), petrolatum (vaseline and petroleum jelly), cera microcrystallina, ozokerite, ceresine and paraffins. Alternatively, synthetic lipids, such as Dimethicone, Cyclomethicone and silicone esters, such as cetearyl methicone can be used. A third alternative is to use animal- or plant-derived lipids, which usually are triglycerides. The naturally animal- or plant-derived lipids are often mixtures of mono-, di- and triglycerides and free fatty acids. The lipids may be purified, hydrogenated, refined, modified and used alone or in different mixtures. Examples of suitable, original animal-derived lipids include bees' waxes, emu oil, lactis lipida, lanolin, shark liver oil and tallow. Examples of suitable plant-derived original lipids include apricot kernel oil, arachis oil, avocado oil/wax, bayberry wax, black currant seed oil, borage seed oil, brazil nut oil, camelia sinensis oil, candelilla wax, canola oil, carnauba wax, castor oil, cocoa butter, coconut oil, corn oil, cotton seed oil, dog rose seed oil, evening primrose seed oil, grape seed oil, illipe butter, jasmine wax, jojoba wax, lavender wax, linseed oil, mango seed oil, olive oil, orange wax, palm oil, palm kernel oil, peanut oil, rice wax, safflower oil, sesame seed oil, shea butter, soybean oil, sunflower seed wax, sweet almond oil and wheat germ oil. The lipids can be used alone or in mixtures comprising at least two lipids.

Preferably, a liquid lipid is used in the present invention. More preferred lipids include olive oil, canola oil, coconut oil, palm kernel oil, peanut oil, soy bean oil, Dimethicone, paraffin oil, and petrolatum. These lipids are especially preferred because they provide high survival of lactic acid bacteria and high transfer rates of the bacteria to the skin and urogenital area. In addition, these lipids have positive effects on the skin; they have a soothing effect, show skin-protective properties, and are non-toxic and non-allergenic. The preferred lipids are all of non-animal origin.

In order to protect the probiotic bacteria from moisture during storage and transportation, the hygiene tissue is preferably provided individually packed in a moisture impervious packing unit. The packing unit can be constructed in several different ways. The material used preferably should not have a vapor permeability exceeding 6 g/m.sup.2/calendar day in accordance with ASTME 398-83 at 37.8.degree. C. and 90% relative humidity. Suitable materials to be used to obtain an impervious packing unit include polyethylene, polypropylene, polyester, polyamide, polyvinylalcohol and similar polymers, aluminum foil, aluminum oxide, silicon oxide, and the like. In order to produce packing material that has good wear strength and can readily be sealed, a less expensive material may be used as outer protective wear layers and/or as inner sealing layers. For instance, the packing unit can comprise an inner material that enables a good seal to be obtained, e.g., polyethylene, polypropylene, butyl acrylate, vinyl acetate or wax, an intermediate material that consists of a moisture impervious material, and a stronger outer barrier material, e.g., polyethylene or polypropylene. After placement of the hygiene tissue comprising the lipid suspension containing the lactic acid producing bacteria, openings of the packing unit are tightly sealed. In an exemplary embodiment, the seals do not have a moisture permeability exceeding that of the packing material itself. Further details on the design of suitable impervious packing units are given in WO00/76878, which hereby is incorporated as reference.

EXAMPLES

Example 1

Survival of *Lactobacillus plantarum* 931 in Olive Oil on Hygiene Tissues

A preparation of freeze dried *L. plantarum* 931 cells in skimmilk was ground until a powder of fine grains was formed. 10 g of the *L. plantarum* 931 powder was added to 120 ml olive oil (Filippo BERIO® extra virgin olive oil) and shaken until a homogenous solution was formed. An additional aliquot of 80 ml of olive oil was added and the resulting 200 ml solution was vortexed for about 2 min. The bacterial suspension was kept at room temperature for 3 hours, with mixing twice an hour. Tissue sheets (Spun Lace Dupont and SCA Absbond) were cut to 6.times.4 cm squares and placed in sterile stainless steel trays. On each tissue sheet, 2 ml of bacterial suspension was dropped over the tissue to cover it. The tissue sheet was folded in the middle, then from the long side to the middle again and packed in foil bags, which edges were welded. Samples were removed for determination of initial bacterial concentration and the remaining bags were stored at room temperature for viability studies.

As a comparison to storage of *L. plantarum* 931 cells in olive oil, *L. plantarum* 931 cells were stored in suspensions of water and olive oil on hygiene tissues. These were prepared by mixing vigorously 2.5 g of freeze dried *L. plantarum* 931 cells (prepared as described above) with 45 ml of Milli Q water and 5 ml olive oil (Filippo BERIO, Italy) or 35 ml Milli Q water and 15 ml olive oil to prepare suspensions with approximately 10 or 30% oil, respectively. The bacterial oil-water suspensions were applied to tissue sheets (Spun Lace Dupont) for bacterial survival studies. On each tissue sheet (6.times.7 cm), 1 ml of bacterial suspension was dropped to cover the tissue. The tissue sheet was folded in the middle, then from the long side to the middle again and packed in foil bags, which edges were welded. Samples were removed for determination of initial bacterial concentration and the remaining bags were stored at room temperature in the dark for viability studies.

To test the viability of the *L. plantarum* 931 cells after storage for different time periods on a tissue sheet, the tissue sheet was transferred to a Stomacher bag and 10 ml of 0.9% NaCl was spread over the tissue sheet. The bag was run for 3 minutes on high effect in the Stomacher bag. The contents of the bag was then transferred to test tubes, diluted in 0.9% NaCl when necessary, and immediately plated onto Rogosa plates. The number of colonies was counted after 2 days of incubation at 37.degree. C. in 5% $CO_2$ in air. Two tissue sheets were analyzed at each sampling date.

Figure 2:
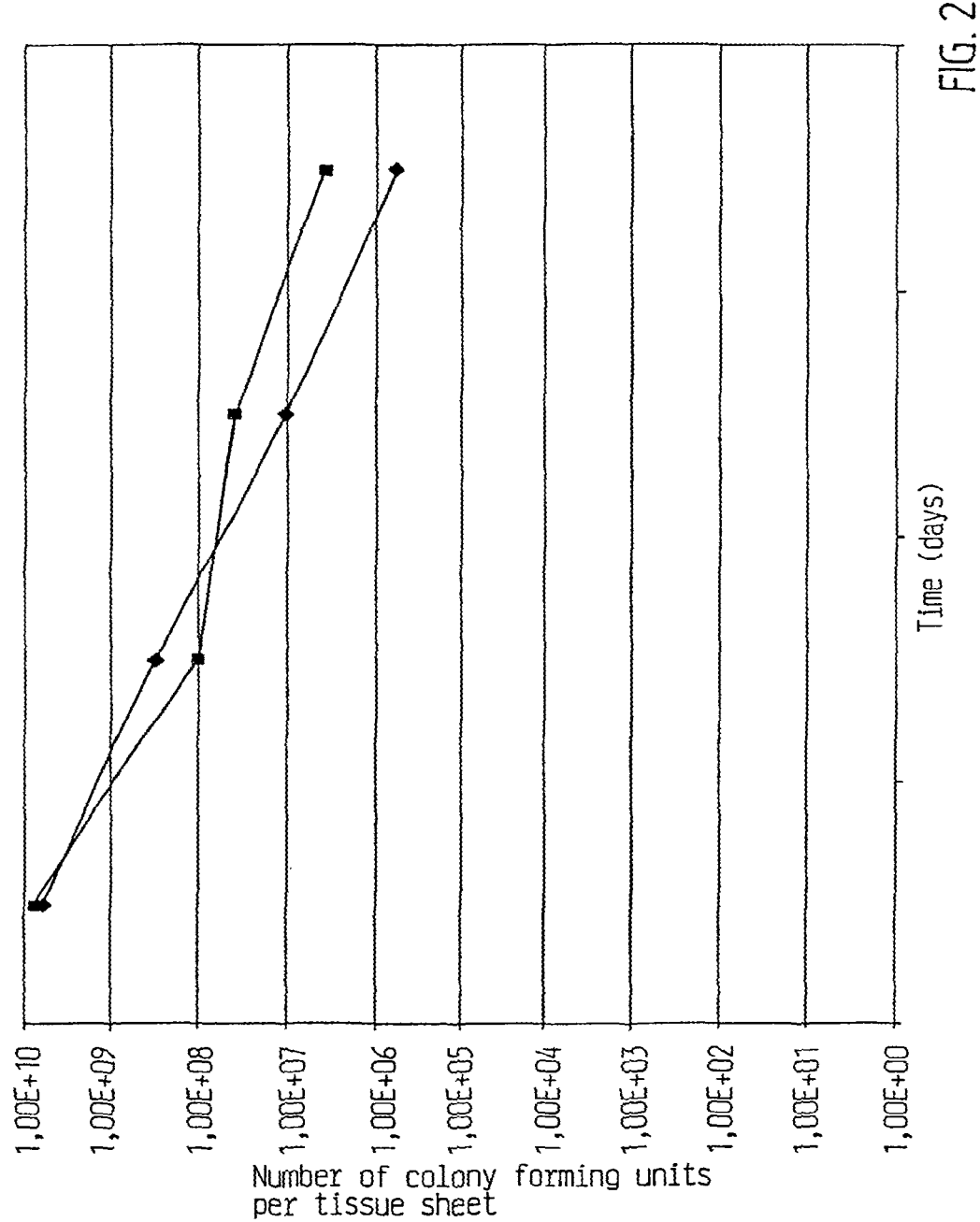
FIG. 2 shows the survival of *Lactobacillus plantarum* 931 in suspensions of water and olive oil on hygiene tissues (Spun Lace Dupont). (.diamond-solid.) 10% olive oil in water, (.box-solid.) 30% olive oil in water.

The survival of L. plantarum 931 in olive oil on hygiene tissues for a total time period of one year and three months is shown in FIG. 1. The survival of the L. plantarum 931 cells stored under these conditions was very high for both tissue sheets variants tested. In comparison, storage of oil-water suspensions (10 and 30% olive oil in water) of the bacteria on a tissue sheet (FIG. 2) resulted in a rapid decrease in viability with a drop of more than $10^3$ orders of magnitude over just a three months time period studied.

Example 2

Survival of L. plantarum 931 in Lipids with Different Chemical Compositions 497 mg of a powder of L. plantarum 931 in skim milk, prepared as described in Example 1, was mixed with 5 ml of olive oil (Filippo BERIO® extra virgin olive oil, Filippo BERIO, Italy) or rapeseed oil (Felix AB, Sweden). The pH of the oils was about 5. The rapeseed oil also contained, in addition to rapeseed oil, citric acid and vitamin A and D. The suspensions were vortexed for 1 minute and allowed to rest for 1 minute. This was repeated four more times. The bacterial suspensions were kept for 4 hours at room temperature with mixing twice an hour. The suspensions were then divided into 1 ml aliquots and stored in sterile brown glass vials. The initial concentrations of bacteria in the suspensions were determined. The vials were stored in a dark place at room temperature and normal air humidity varying from 30-60%.

In addition to the experiment described above, to further compare the survival of L. plantarum 931 in lipids with different compositions, 2 g of freeze-dried L. plantarum 931 cells in skimmilk ($2 \times 10^{10}$ colony forming units/g) were mixed with either 40 ml or 40 g of the different lipid compositions, depending on the lipid consistency. The tested lipids were: white vaseline (petrolatum, Apoteket AB, Umea, Sweden), paraffin (paraffinum liquidum, Apoteket AB, Gothenburg, Sweden), glycerol ("glycerin", maximum water content 0.5%, Apoteket AB, Gothenburg, Sweden), olive oil ("*Olea Europea*", cold pressed, Apoteket AB, Gothenburg, Sweden), dimethiconum (Dimethicone, 350 cSt., Dow Corning 200/350 S fluid, Kebo Lab, Sweden), and Akoline MCM (mono-diglyceride of medium chain fatty acids; primarily caprylic and capric acids, Karlshamns AB, Sweden), Akomed R (caprylic/capric triglyceride from coconut and/or palm kernel oils, deodorized, Karlshamns AB, Sweden), and Akorex L (canola oil, partially hydrogenated, deodorized, Karlshamns AB, Sweden). The samples were stored in sterile, brown, glass vials at room temperature in the dark at normal air humidity (varying from 30-60% relative humidity). To establish the number of viable L. plantarum 931 cells after different storage times, 1 g of the samples was transferred to a stomacher bag and 9 ml of 0.9% NaCl was added. The bag was then run at high effect in Stomacher for 3 minutes. The contents of the bag was transferred to test tubes, diluted when necessary in NaCl and cultured on MRS-plates at 37.degree. C. in 5% $CO_2$ in air for 2 days.

As a comparison to storage of L. plantarum 931 cells in different lipids, L. plantarum 931 cells were also stored in suspensions of water and olive oil. These were prepared by mixing vigorously 2.5 g of freeze dried L. plantarum 931 cells (prepared as described above) with 45 ml of Milli Q water and 5 ml olive oil (Filippo BERIO, Italy) or 35 ml Milli Q water and 15 ml olive oil to prepare suspensions with approximately 10 or 30% oil, respectively. The samples were stored in sterile plastic vials at room temperature at normal air humidity (varying from 30-60% relative humidity). To test survival after different time intervals, samples were removed from the vials, diluted in 0.9% NaCl and incubated at 37.degree. C. in 5% $CO_2$ in air for 2 days.

Figure 3:
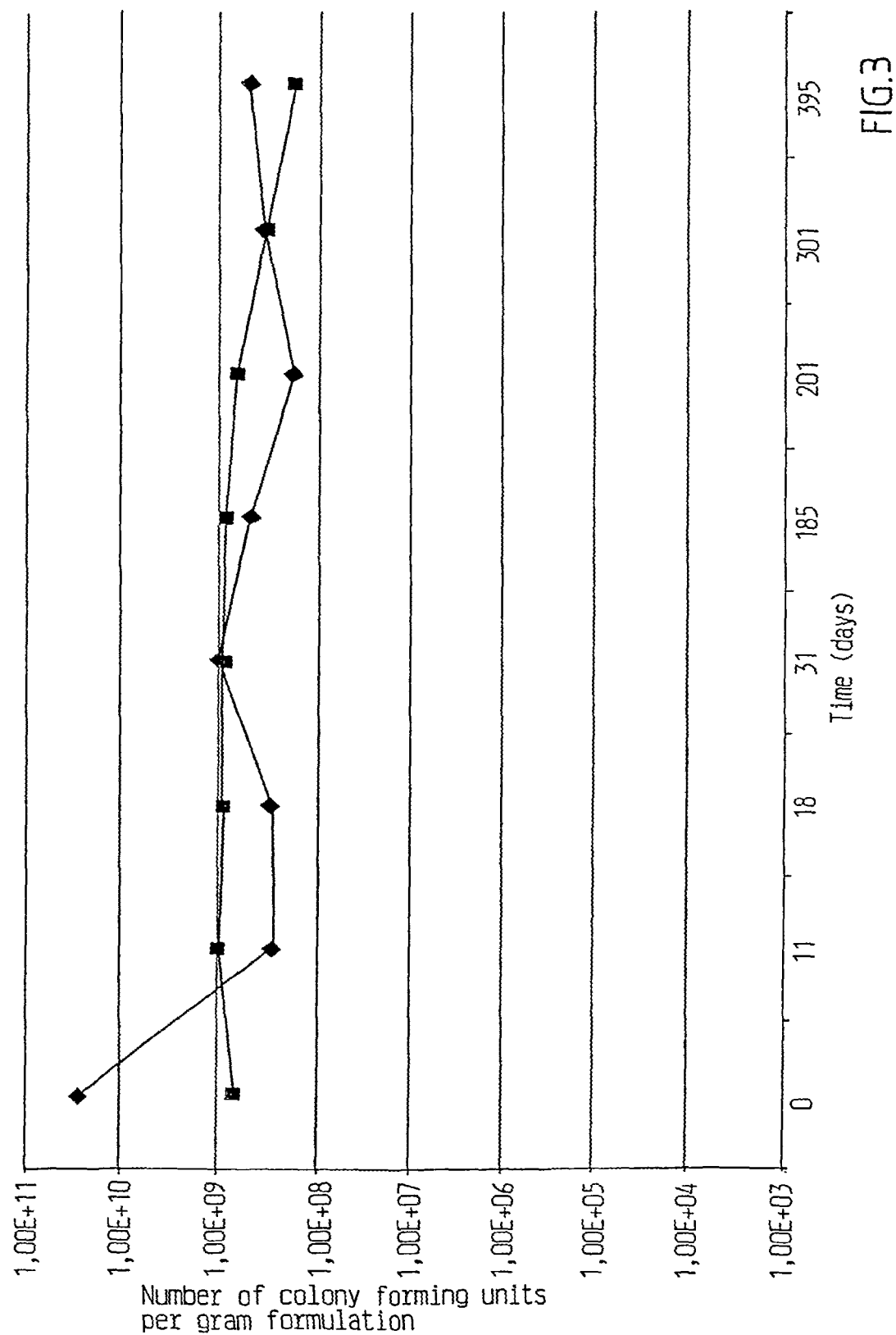
FIG. 3 shows the survival of *Lactobacillus plantarum* 931 in olive (.diamond-solid.) and rapeseed (.box-solid.) oil.
Figure 4:
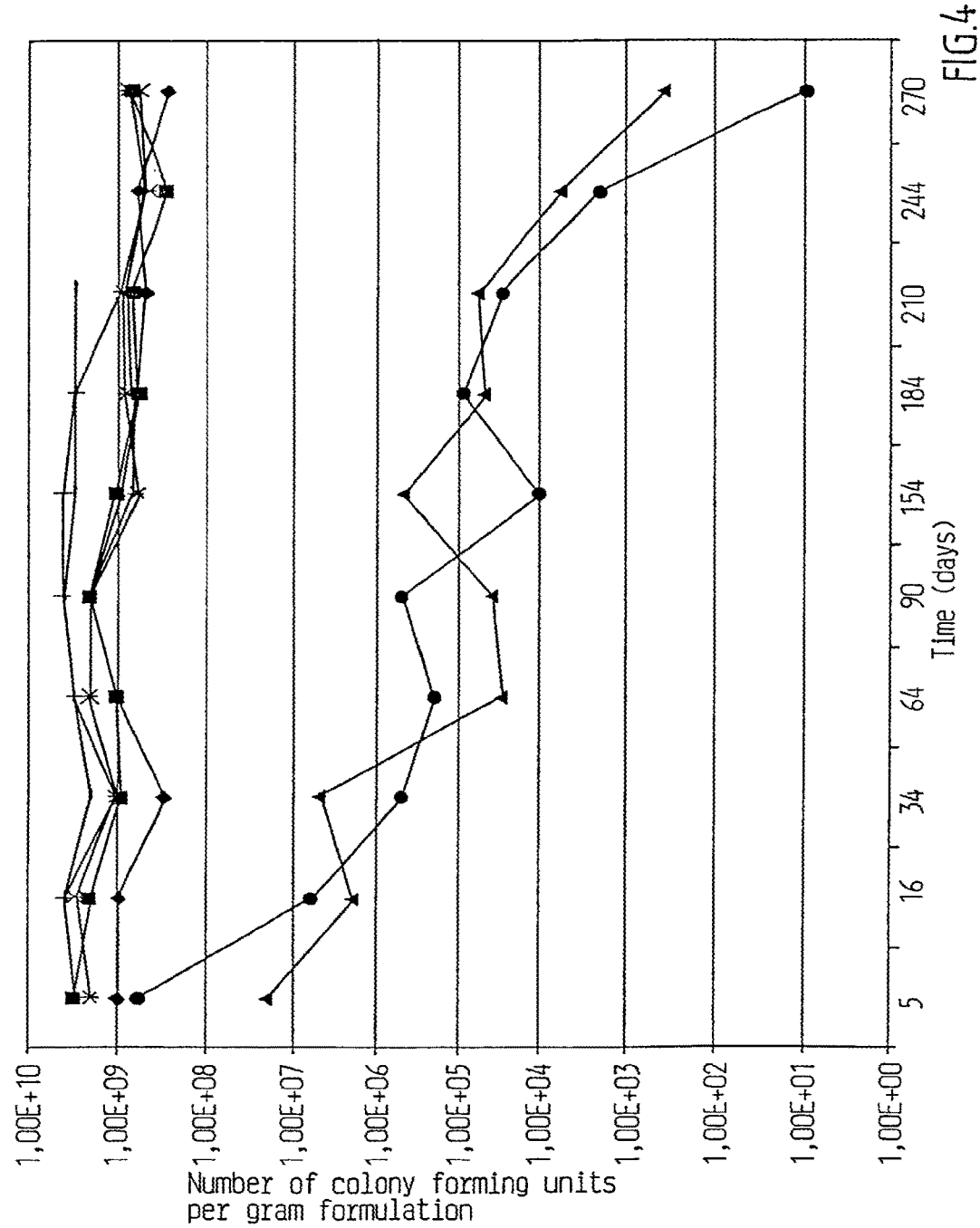
FIG. 4 shows the survival of *Lactobacillus plantarum* 931 in lipids with different chemical compositions. (.diamond-solid.) vaseline, (.box-solid.) paraffin, (.tangle-solidup.) glycerolum, (x) olive oil, (*) Dimeticonum, (.circle-solid.) Akoline MCM, 0 Akomed R, (.sup.-) Akorex L.
Figure 5:
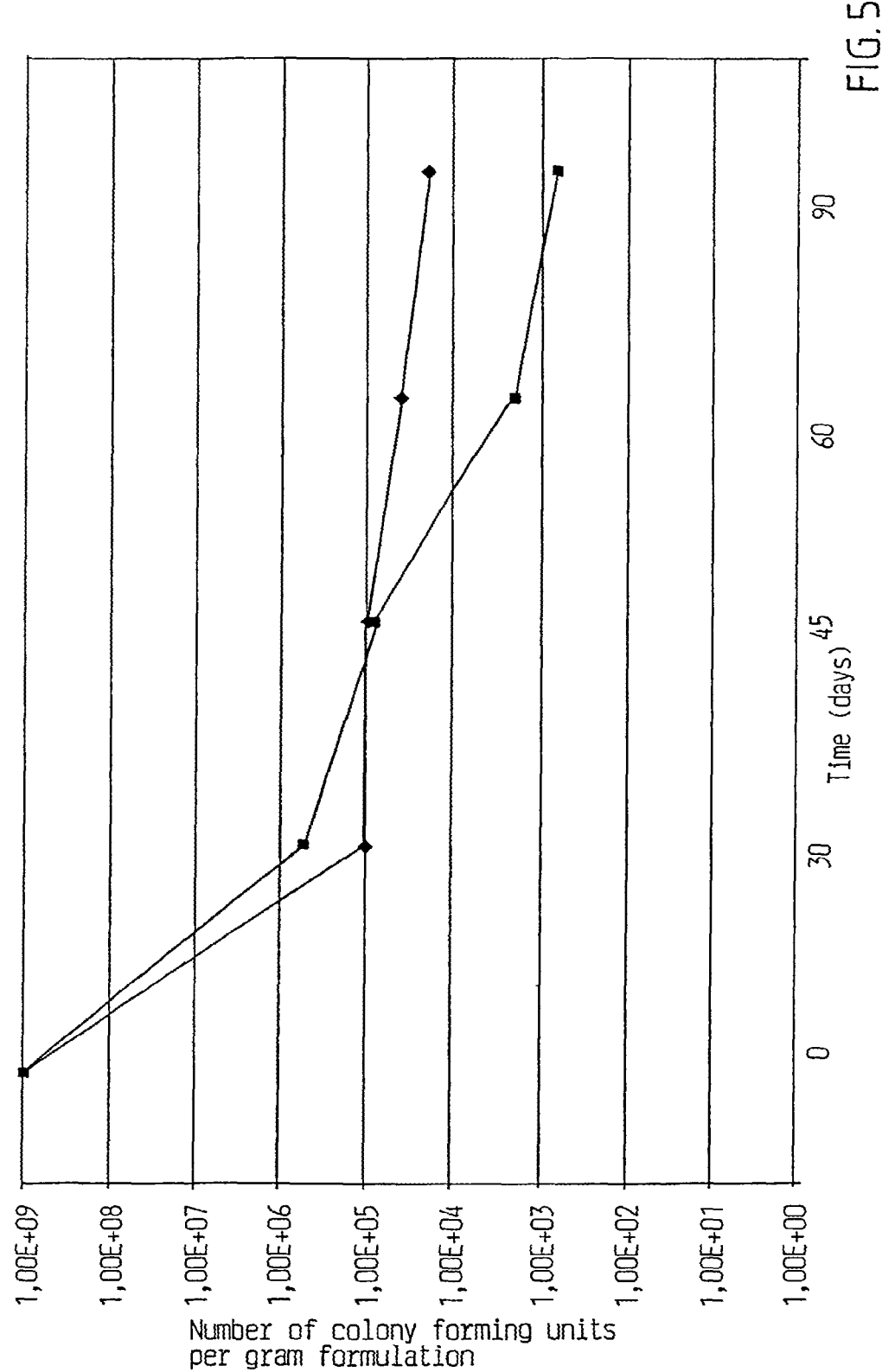
FIG. 5 shows the survival of *Lactobacillus plantarum* 931 in suspensions of water and olive oil. (.diamond-solid.) 10% olive oil in water and (.box-solid.) 30% olive oil in water.

FIG. 3 shows the level of survival of the L. plantarum 931 cells in olive and rapeseed oil over the more than one year time period studied. Storage in vaseline, paraffin, Dimeticonum, Akoline MCM, Akomed R, and Akorex L also resulted in survival over extended time periods (FIG. 4). However, storage in the more hydrophilic glycerol resulted in a decrease in survival over time (FIG. 4). Also, the Akoline MCM, known to have bacteriostatic properties, could not support survival of the cells (FIG. 4). In addition, it can be seen that storage in the more hydrophilic environment provided in the oil-water suspensions (FIG. 5) results in a very rapid initial decrease in viability by more than $10^2$ orders of magnitude over the first month of storage. During the next two months studied, the decrease in survival rates flattened out, but still the decrease in survival is much higher than what is observed when the bacterial cells were stored in a lipid.

Example 3

Study on Transfer Efficacy to and Survival Rates on Skin of L. plantarum 931 Suspended in Olive Oil, Paraffin Oil or Milli Q Water 2.00 g of freeze-dried L. plantarum 931 were added to a sterile glass vial and 40 ml of olive oil, paraffin oil or Milli Q water were added. The suspensions were shaken until homogenous solutions formed and were left at room temperature for four hours. Tissue sheets with L. plantarum 931 were prepared by cutting tissue sheets to $7 \times 8$ cm pieces and dropping 2 ml of the different bacterial suspensions, prepared as described above, to cover the tissue. The tissue sheets were folded in the middle, then from the long side to the middle again and packed in foil bags which edges were welded. Samples were removed for determination of initial bacterial concentrations and the remaining bags were stored at room temperature for viability studies. Two of the prepared tissue sheets with L. plantarum 931 for each preparation were used in the bend of the arm on five subjects (i.e., one tissue was used for three subjects and the other one for two). Before the test, samples were taken to assure that no L. plantarum 931 cells were initially present on the skin. On each subject, in one bend of the arm a tissue sheet with L. plantarum 931 in Milli Q water was streaked and a tissue sheet with L. plantarum 931 in olive oil was similarly used in the other. The skin was then sampled for presence of L. plantarum 931 cells at 0, 4, 6 and 24 hours after streaking. The sampling procedure was as follows: a sterile stick provided with a cotton wool top was dipped in 0.9% NaCl and rolled 4 times over an area of 1 $cm^2$ at the site of application of the bacteria. The stick was then dipped in 1 ml of 0.9% NaCl and mixed. The samples were diluted in 0.9% NaCl and immediately plated onto Rogosa plates. The plates were incubated at 37.degree. C. in 5% $CO_2$ in air for 2 days. After 24 hours the bend of the arm, where *L. plantarum* 931 cells in Milli Q water were applied, was rinsed with Sumabac (Diversey Lever, Huddinge, Sweden) and a tissue sheet with *L. plantarum* 931 cells in paraffin oil was streaked in that bend of the arm, which, as previously, was sampled at 0, 4, 6 and 24 hours after streaking to assess the amount of *L. plantarum* 931 cells on the skin.

Figure 6:
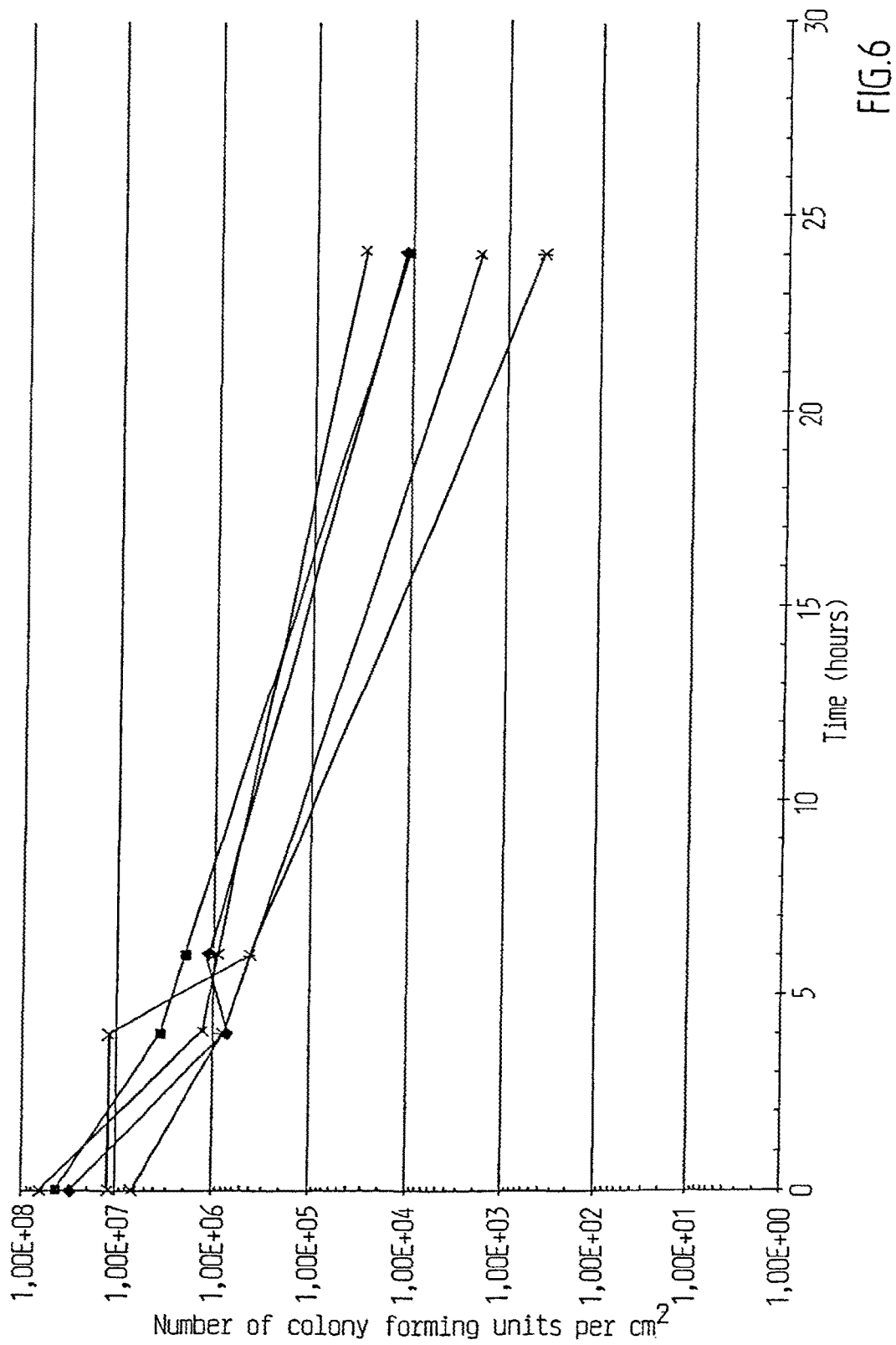
FIG. 6 shows transfer efficacy to and survival rate on skin of *Lactobacillus plantarum* 931 suspended in olive oil on hygiene tissues used on five different subjects.
Figure 7:
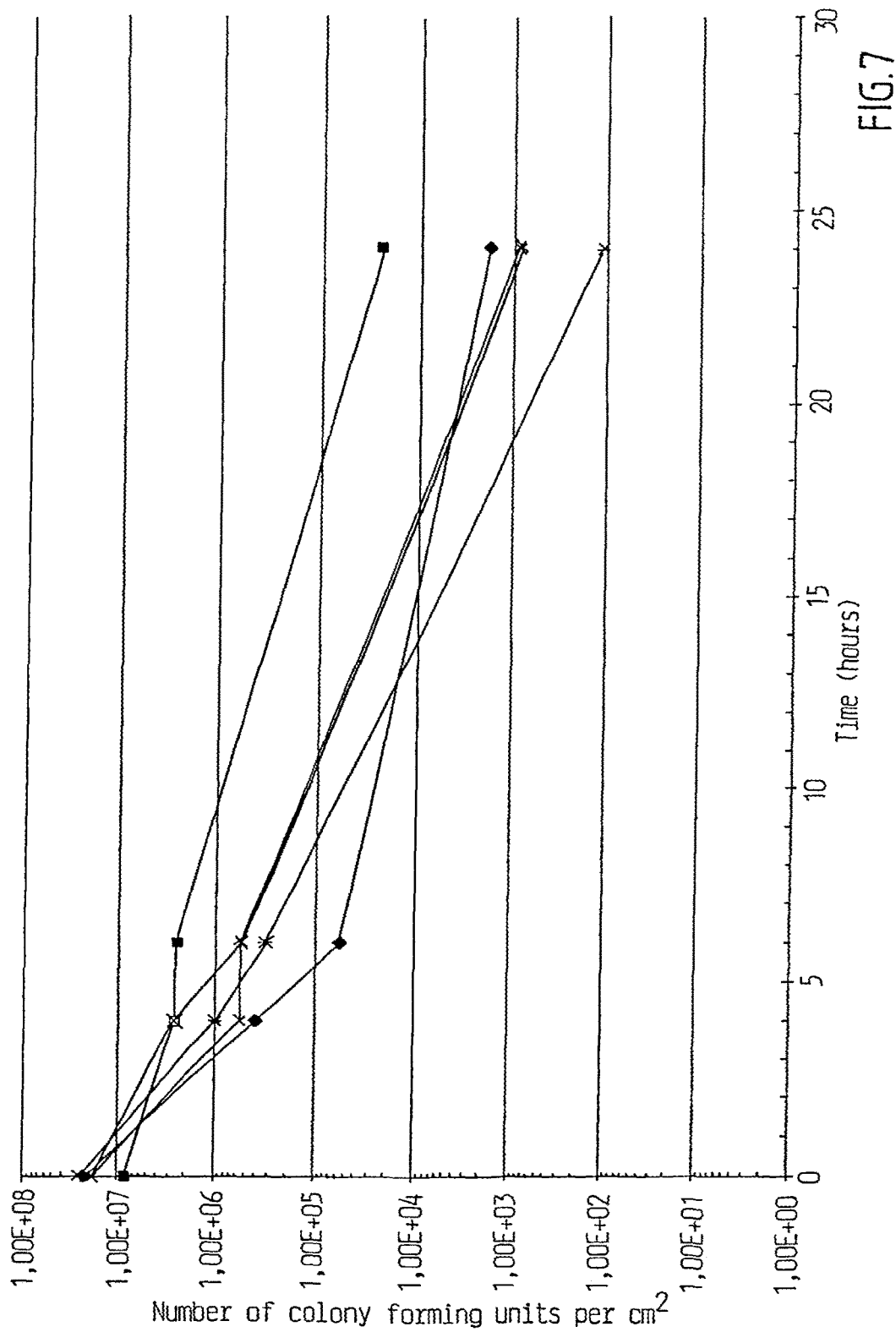
FIG. 7 shows transfer efficacy to and survival rate on skin of *Lactobacillus plantarum* 931 suspended in paraffin oil on hygiene tissues used on five different subjects.
Figure 8:
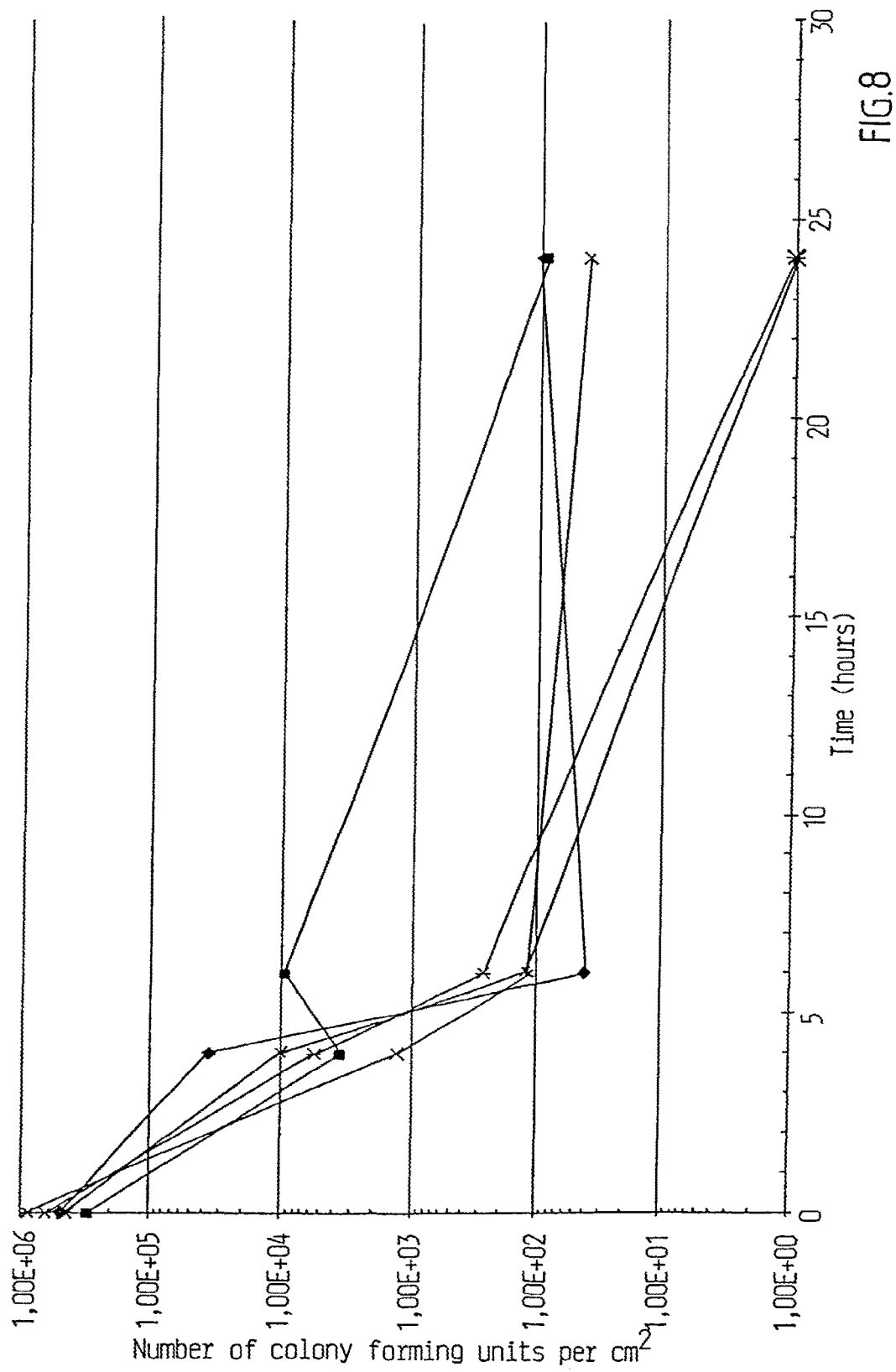
FIG. 8 shows transfer efficacy to and survival rate on skin of *Lactobacillus plantarum* 931 suspended in Milli Q water on hygiene tissues used on five different subjects.

As shown in FIGS. 6-8, the amount of *L. plantarum* 931 cells transferred to the skin was usually more than 10 times higher when the bacteria were suspended in olive (FIG. 6) or paraffin oil (FIG. 7) compared to when they were suspended in Milli Q water (FIG. 8). Suspending the bacteria in lipid instead of water therefore was demonstrated to enhance the transfer rate of the bacteria to the skin. Also, once the *L. plantarum* 931 cells were on the skin, the lipid also enhanced bacterial survival, since the initial drop in bacterial counts was slower and the final level of bacteria on the skin after 24 hours was higher after use of a tissue where the bacteria were suspended in olive or paraffin oil (FIGS. 6 and 7), compared to what was found when water was used as suspending agent (FIG. 8).

Example 4

Transfer of *L. plantarum* 931 Suspended in Olive Oil Applied to a Tissue Sheet Used in the Urogenital Area A bacterial suspension was prepared by adding 5.051 g of a powder of *L. plantarum* 931 (prepared as described in Example 1) to 100 ml olive oil (Filippo BERIO® extra virgin olive oil). The powder was first added to 75 ml of olive oil and shaken to form a homogenous solution before addition of another 25 ml, followed by vortexing for 2 min. The bacterial suspension was kept at room temperature for 2 hours, with mixing twice an hour. A tissue sheet was prepared and inoculated with the bacteria as described in Example 1. Four girls were treated with the tissue sheet in the urogenital area. Samples were collected from the urethra and perineum, using sterile cotton sticks, before using the tissue sheet, to ensure that no lactobacilli were initially present. Thereafter samples were collected immediately after treatment, and after 2, 4, 6, and 17 hours, to monitor transfer and survival of the lactobacilli by dipping a sterile stick provided with a cotton wool top in MRS-broth and rolling it three times over an area of 1 cm.sup.2 at the site of application of the bacteria. The stick was then put in one ml MRS-broth. In the same way a stick was rolled over the uretra over an area of ¼ cm.sup.2 and was the put in another tube of MRS-broth. The samples were plated onto Rogosa plates containing 128.mu.g/ml vancomycin. The plates were incubated at 37.degree. C. in 5% CO.sub.2 in air for two days.

Figure 9:
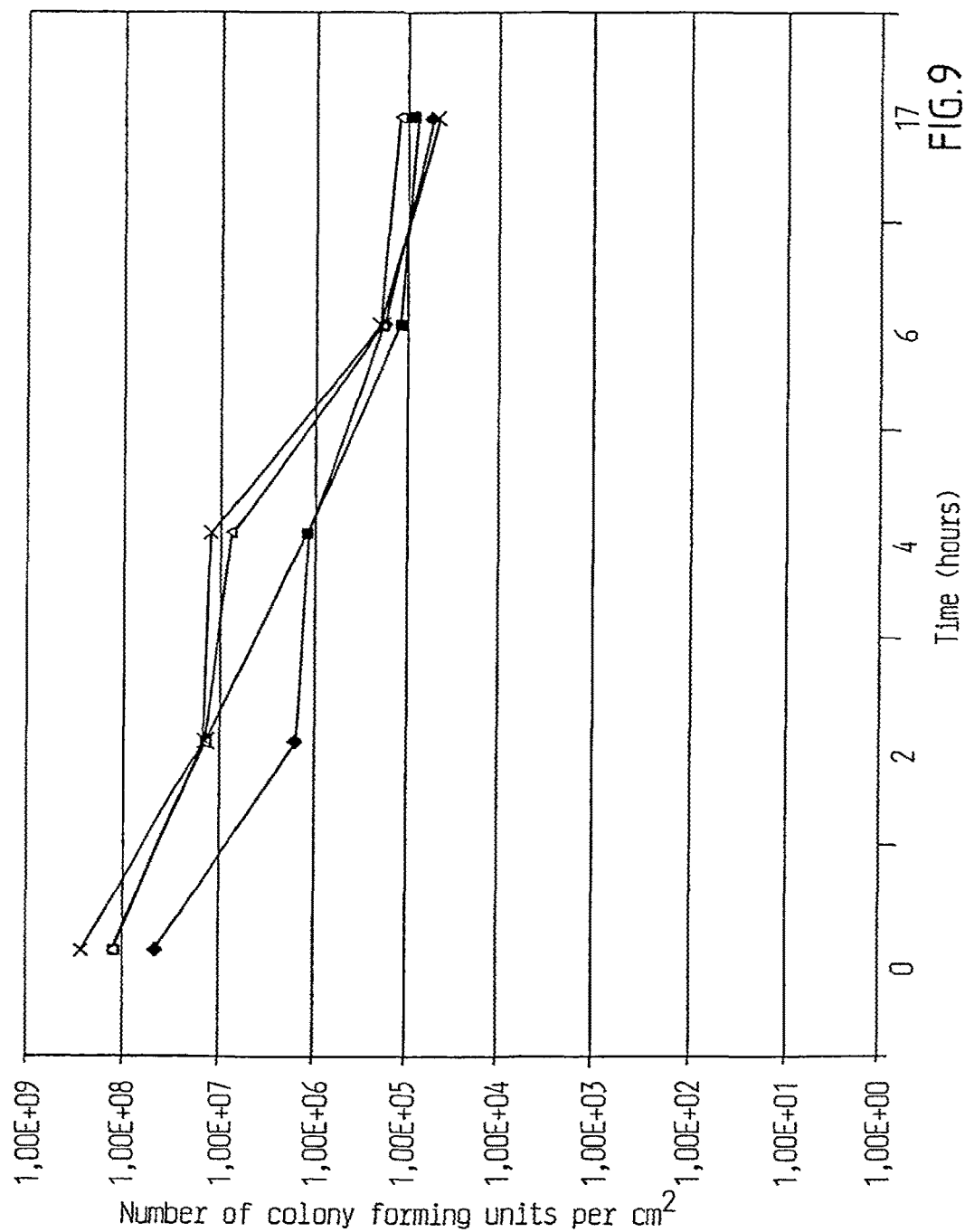
FIG. 9 shows transfer to and survival of *Lactobacillus plantarum* 931 suspended in olive oil in the urethra after application via a tissue sheet used in the urogenital area on four different subjects.
Figure 10:
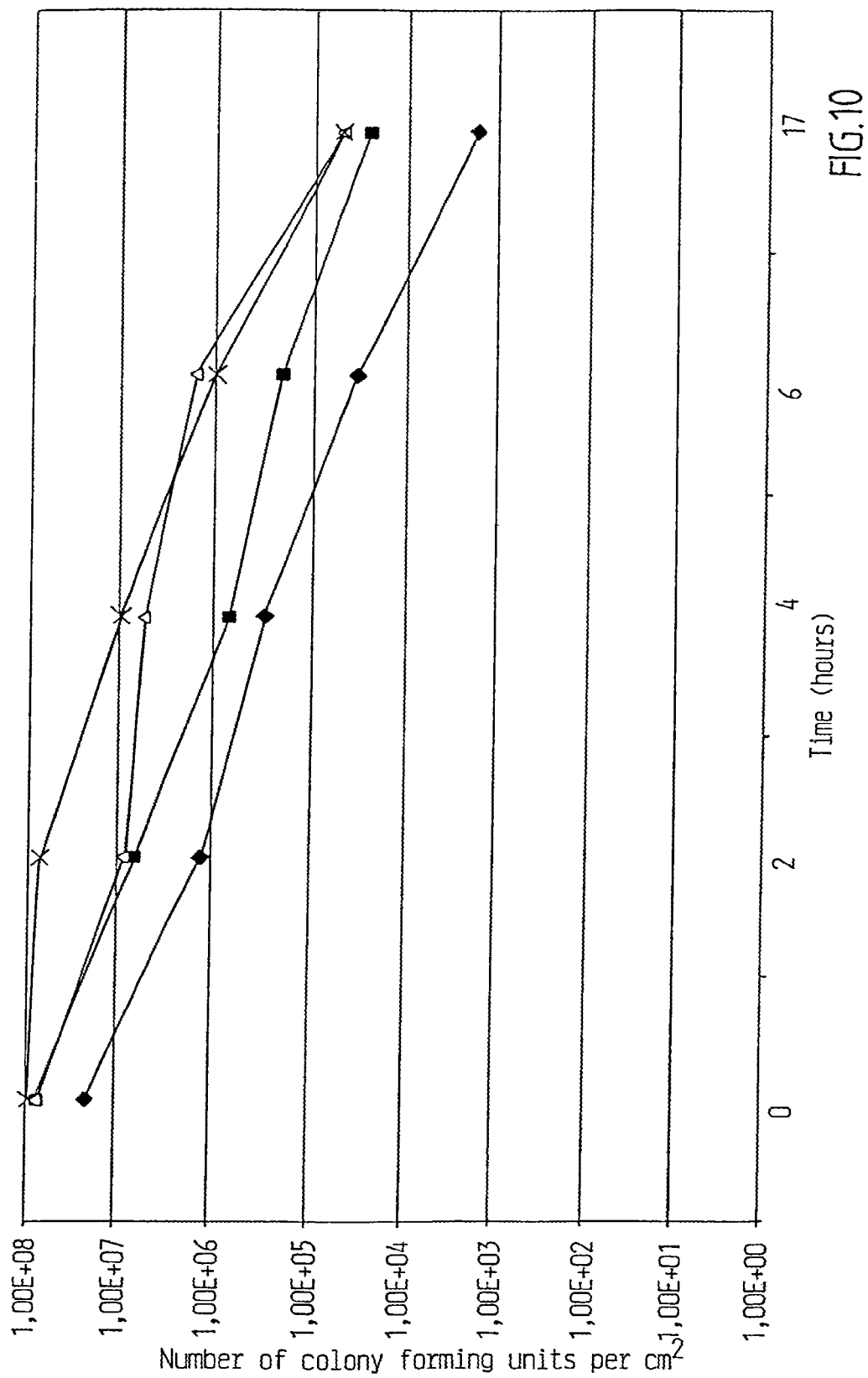
FIG. 10 shows transfer to and survival of *Lactobacillus plantarum* 931 suspended in olive oil in the perineum after application via a tissue sheet used in the urogenital area on four different subjects.

The girls were not allowed to take a bath or shower during the study, but were not given instructions in any other respect. The results shown in FIGS. 9 and 10 demonstrate that there was a high level of transfer of *L. plantarum* 931 to the urethra (FIG. 9) and perineum (FIG. 10) and that a surprisingly high amount of bacteria remained in these areas during the time period studied.

Example 5

Viability of *L. plantarum* 931 after Storage in Olive Oil on a Hygiene Tissue

Figure 11:
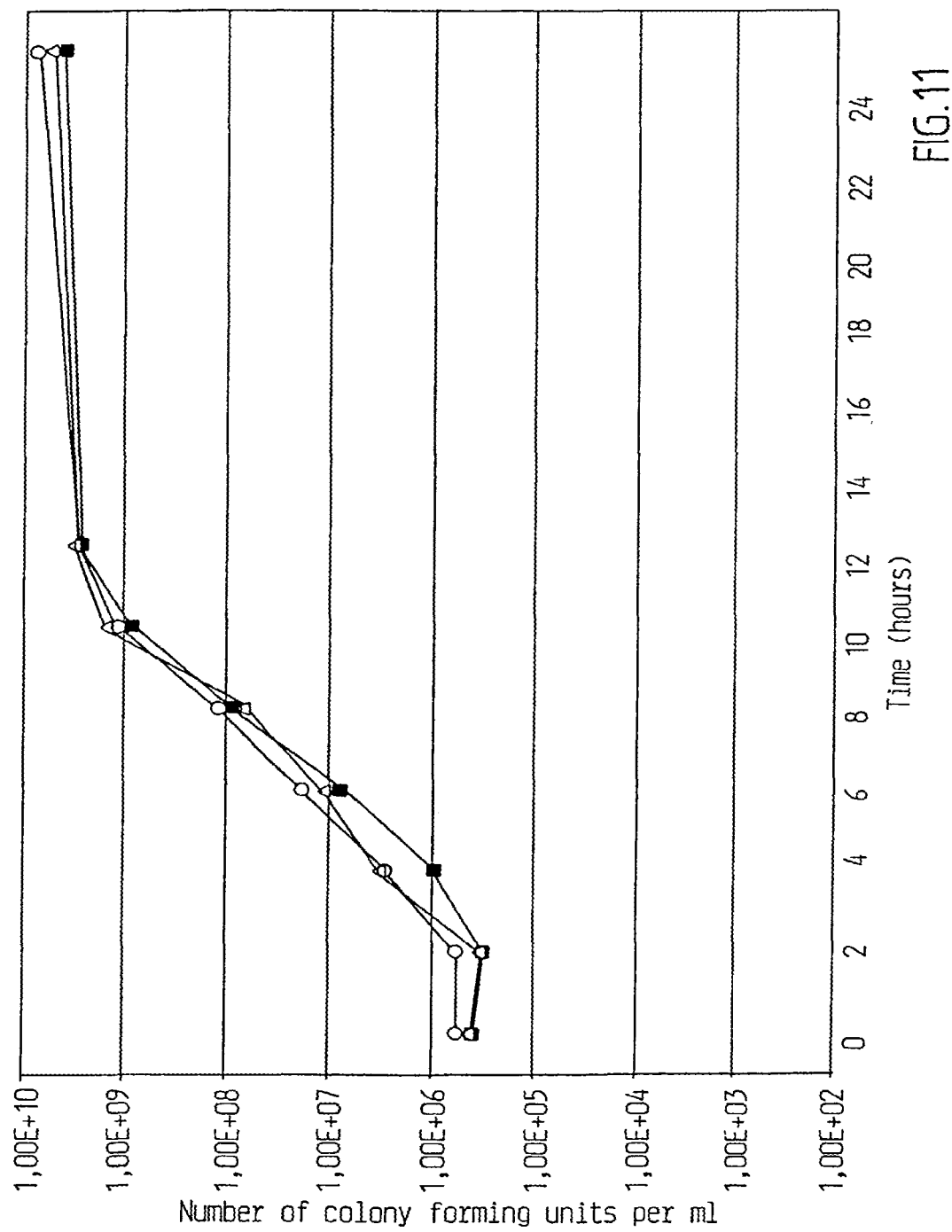
FIG. 11 shows the growth rate of *Lactobacillus plantarum* 931 cells after storage in olive oil on a tissue sheet (.DELTA. and .largecircle.) as compared to the growth rate of freshly inoculated *L. plantarum* 931 cells from an overnight culture (.box-solid.).

Growth of *L. plantarum* 931 suspended in olive oil on tissue sheets that had been stored for 6 days was compared to growth of *L. plantarum* 931 that were not suspended and stored in olive oil. The tissue sheets were wetted with 10 ml 0.9% NaCl and run in Stomacher for 3 minutes on high effect. The solution was then transferred to test tubes and 10 ml were inoculated into 10 ml MRS broth. The bacterial concentration was followed during growth at 37.degree. C. in 5% CO.sub.2 in air by quantifying the number of colony forming units (CFU) and the optical density (OD) at 0, 2, 4, 6, 8, 10, 12 and 24 hours. Duplicate samples were taken for the analysis. The results shown in FIG. 11 demonstrate that the capability of growth of the *L. plantarum* 931 cells had been suspended and stored in olive oil on a tissue sheet is just as good as growth of cells from an overnight culture of *L. plantarum* 931. Accordingly, the *L. plantarum* 931 cells were not negatively affected by the storage in olive oil.

Example 6

Difference in Transfer Rates and Maintenance Levels of LB931 and ATCC 8014 Provided Via Panty Liners, in Urethra and Perineum Areas

*Lactobacillus plantarum* strain LB931 (DSM11918) was obtained from Deutche Sammlung von Microoganismen and Zellkulturen, Mascheroder Weg 1b, D-38124 Braunschweg, Germany. *Lactobacillus plantarum* strain ATCC 8014, as described in U.S. Pat. No. 5,705,160, was obtained from America Type Culture Collection, 12301 Parklawn Drive, Rockville, Md. 20852, USA.

LB931 and ATCC were grown on MRS agar plates for two days at 37.degree. C. in CO.sub.2 (5%). One colony of each strain was inoculated into 5 ml of MRS broth (start tube) and incubated in the same way as above, but overnight. 50.mu.l from the start tube was placed into 5 ml of MRS broth, preheated to 37.degree. C., and incubated at 37 degrees C. for eight hours. 500 µl was put in 50 ml of preheated MRS broth and is incubated at 37 degrees C. for 16 hours.

The suspension was centrifuged for 20 minutes at 3000.times.g at 4.degree. C., and the pellet was washed three times in 10-20 ml NaCl (0.9%). After washing, the pellet was resuspended in 2.5 ml NaCl (0.9%)+2.5 ml skim milk, thereby concentrating the sample 10.times. This suspension was transferred to an actuator vial. Each 10+1 (test) panty liners were sprayed with about 150 mg of bacterial suspension. The panty liners were dried for 6 hours at room temperature before being packaged one by one into minigrip bags.

Control of colony forming units (CFU) of the test panty liner: 50 ml of NaCl (0.9%) was poured over the panty liner in a stomacher bag and run at high speed for 3 minutes. The fluid is diluted and 100 µl was spread on MRS agar plates. The number of CFU/panty liner for ATCC 8014 was $3 \times 10^9$ and for LB931 was $1 \times 10^9$.

Women took a time zero sample (perineum and urethra) before wearing a panty liner supplied with either of the *L plantarum* strains for 5 hours. The panty liner was removed and sample 2 was taken. After 24 hours (from time zero sample), sample 3 was taken. Transfer is defined as % of total women that after 24 hours still carry bacteria.

Figure 12:
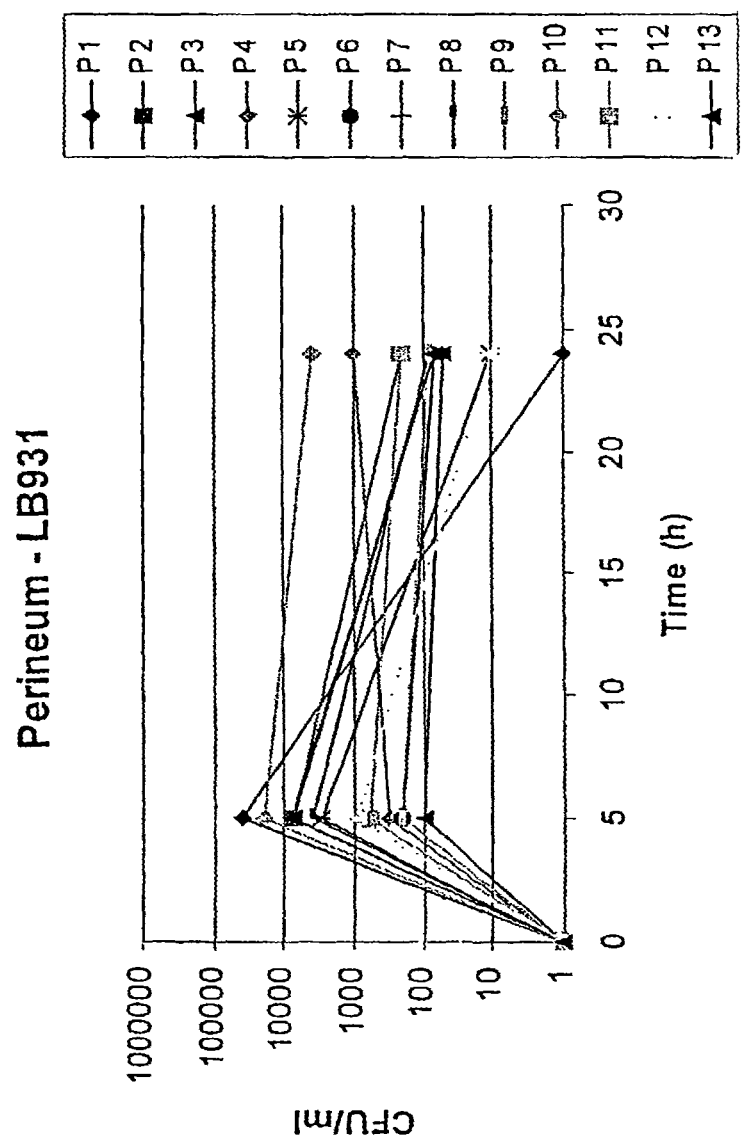
FIG. 12 shows the transfer and maintenance of *Lactobacillus plantarum* 931 in the perineum.
Figure 13:
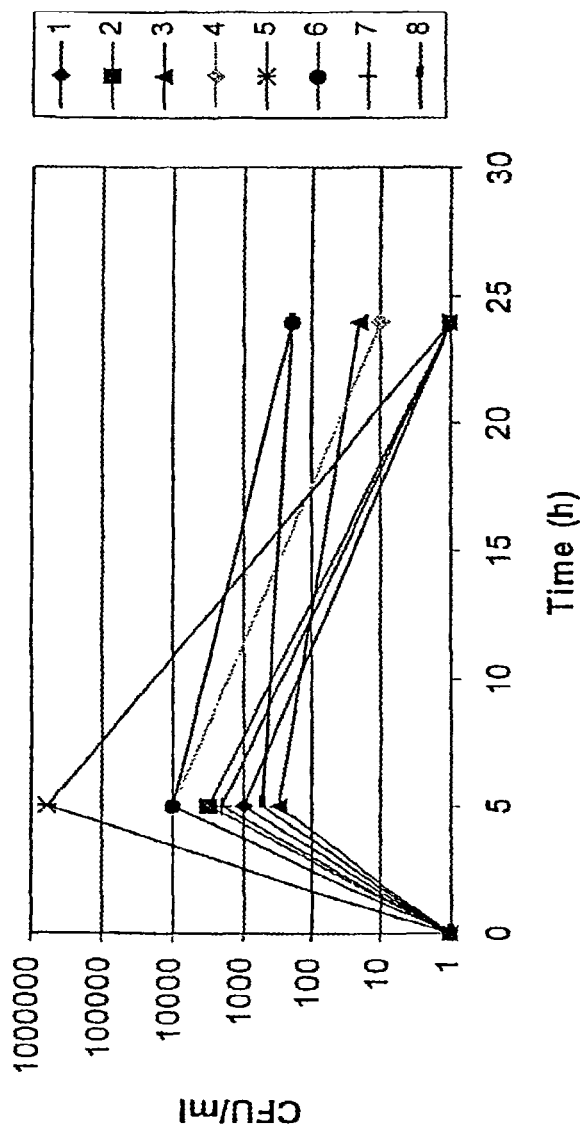
FIG. 13 shows the transfer and maintenance of *Lactobacillus plantarum* ATCC 8014 in the perineum.

As shown in FIG. 12, more of the women who had used panty liners with LB931 still harbored the LB931 bacteria in the perinuem 24 hours after the time zero sample was taken (92% still harbored the bacteria). In comparison, of the women who had used panty liners with ATCC 8014 only 50% harbored the tested bacterial strain at the same time point in the perineum (FIG. 13).

Figure 14:
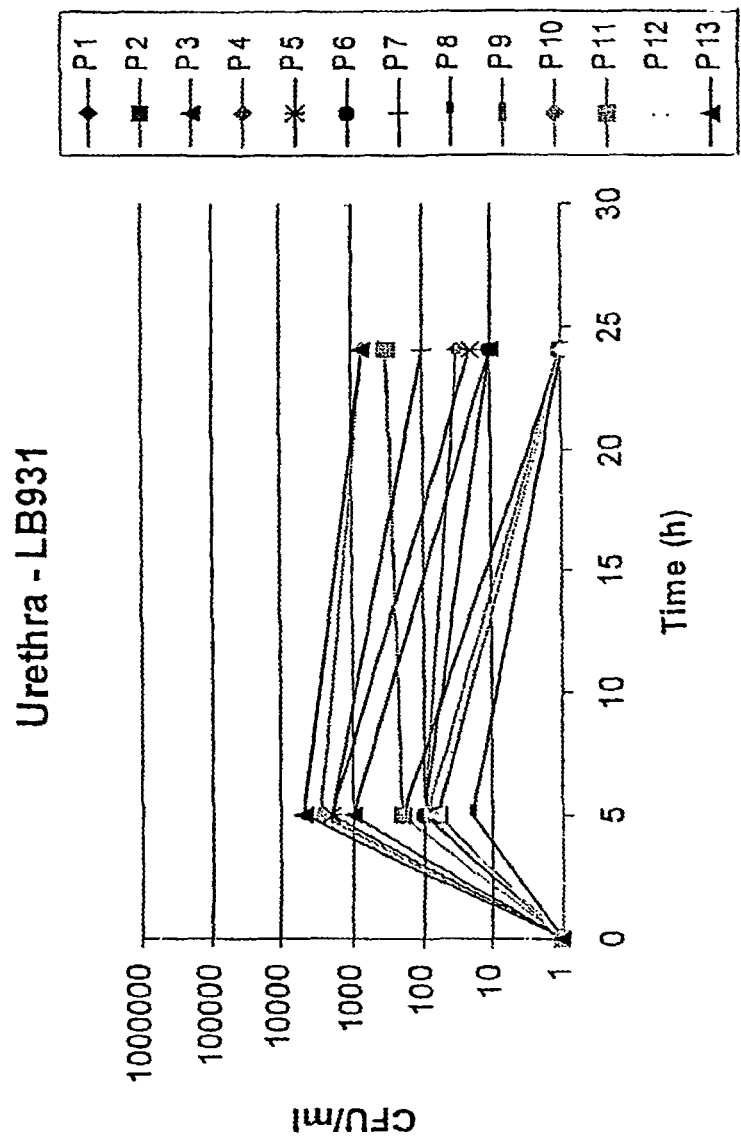
FIG. 14 shows the transfer and maintenance of *Lactobacillus plantarum* 931 in the urethra.
Figure 15:
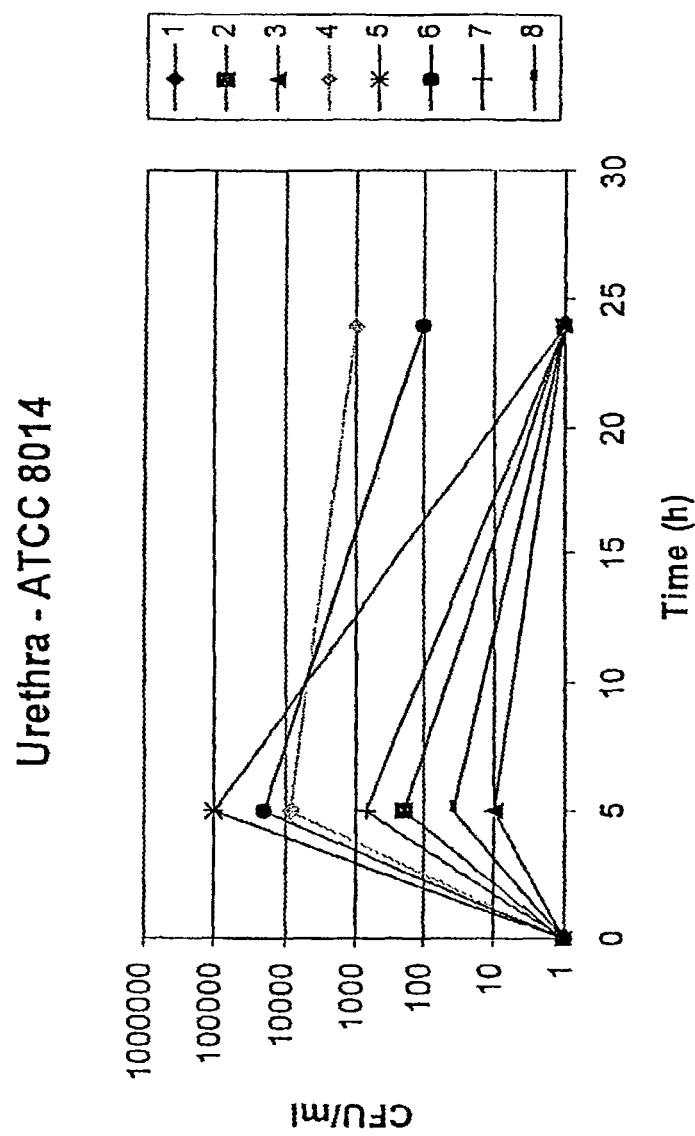
FIG. 15 shows the transfer and maintenance of *Lactobacillus plantarum* ATCC 8014 in the urethra.
Figure 16:
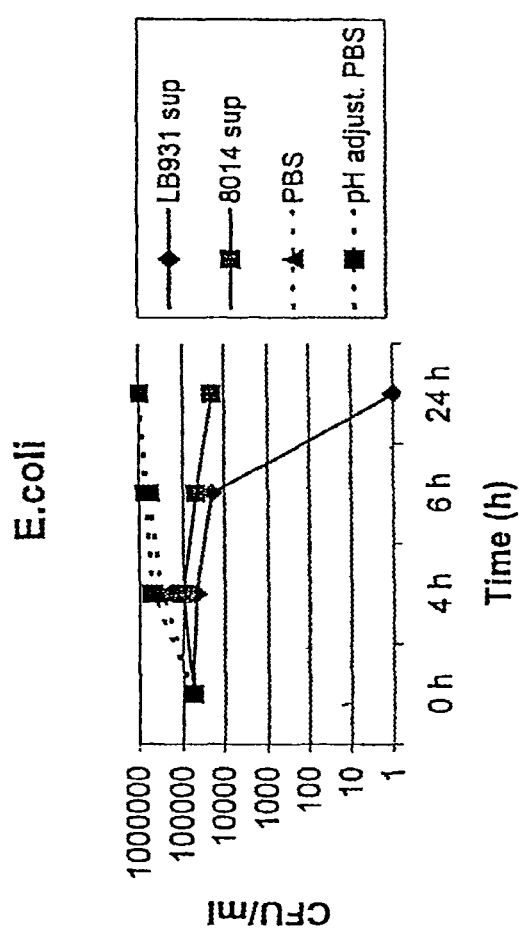
FIG. 16 shows the inhibition of *E. coli* by *Lactobacillus plantarum* LB931 and ATCC 8014.
Figure 17:
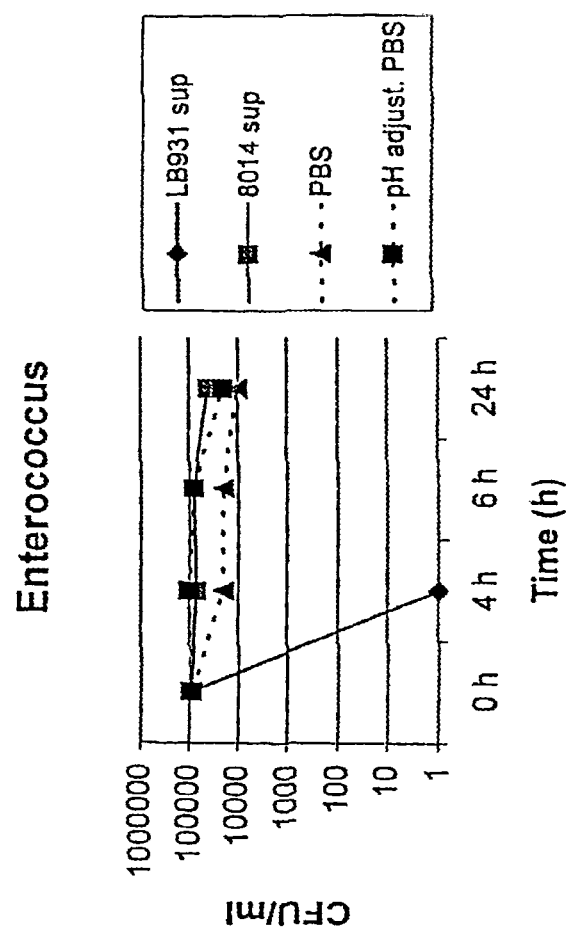
FIG. 17 shows the inhibition of *Enterococcus* by *Lactobacillus plantarum* LB931 and ATCC 8014.
Figure 18:
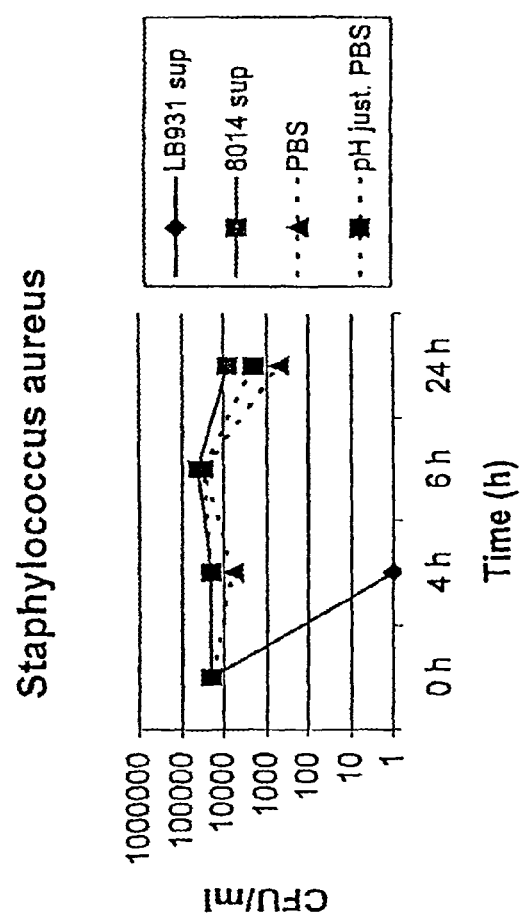
FIG. 18 shows the inhibition of *Staphylococcus aureus* by *Lactobacillus plantarum* LB931 and ATCC 8014.
Figure 19:
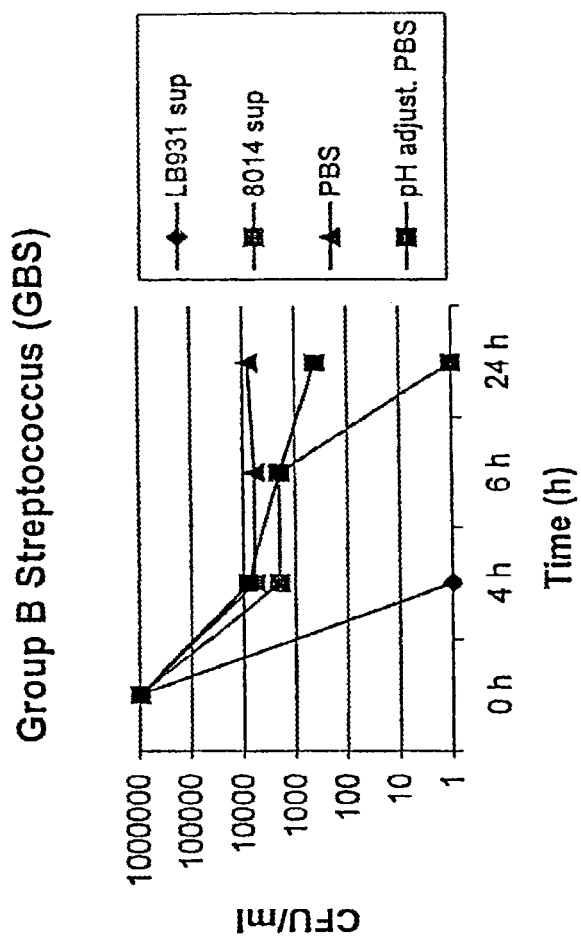
FIG. 19 shows the inhibition of Group B *Streptococcus* by *Lactobacillus plantarum* LB931 and ATCC 8014.

A similar difference was observed when the number of bacteria that still were present in the urethra was determined 24 hours after the time zero sample was taken. In this case, 62% of the women who had used panty liners with LB931 harbored the bacteria (FIG. 14), compared to 25% of women who had used panty liners with ATCC 8014 (FIG. 15).

Example 7

Comparison of Ability of Growth Inhibition and Killing of Pathogenic Bacteria Between LB931 and ATCC 8014

LB931 and ATCC 9014 were grown as described above, but to a final volume of 100 ml each. The suspension was centrifuged and resuspended in 10 ml of PBS, in a Falcon tube (size 50 ml). The tube was incubated at 37 degrees C. for 5 hours. Thereafter the suspension was centrifuged and the supernatant (PBS sup) collected, containing inhibiting substances secreted by the lactic acid bacteria. The PBS sup was stored at −20 degrees C. until use. For controls, PBS buffer, pH adjusted (pH 5.1) and unadjusted (pH 7.3) were used.

The ability of the two tested *Lactobacillus plantarum* strains, LB931 and ATCC 8014, to inhibit growth of common urogential pathogens was tested. The tested pathogens were *Escherichia coli, Enterococcus, Staphylococcus aureus*, and Group B *Streptococcus* (GBS). These bacteria were grown in TH broth and diluted 1:100 before 10 µl was inoculated into 1 ml of PBS sup. The number of pathogens was determined for the tested pathogenic strains at 0, 4, 6, and 24 hours.

As can be seen in FIGS. 16-19, LB931 is superior over ATCC 8014 in inhibiting growth and killing pathogenic bacteria. In the case of *E. coli, Enterococcus*, and *S. aureus*, the growth of these pathogenic strains was not or was only marginally inhibited by the ATCC 8014 strain, while the pathogenic bacteria are completely abolished when placed in the supernatant of LB931. In the case of GBS, LB931 supernatant killed all the bacteria within 4 hours, while ATCC 8014 required 24 hours to do the same.

It is apparent from Examples 6 and 7 that the ability of LB931 to be transferred and maintained in the urogenital area is higher than it is for another *L. plantarum* strain, ATCC 8014. There is a very pronounced difference between the two *L. plantarum* strains in their ability to inhibit growth of and killing pathogenic bacteria, with LB931 being superior over ATCC 8014. Thus, a clear advantage can be gained in using LB931 as a probiotic bacterium in hygiene products such as embodiments of the present invention over other *L. plantarum* strains.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A hygiene tissue comprising a matrix impregnated by a composition, the composition including a probiotic bacterial preparation of one or more lactic acid producing bacterial strains, the lactic acid producing bacterial strains encapsulated in a lipid phase comprising one or more lipids which are all of a non-animal origin,
   wherein the matrix of the hygiene tissue has a water content of 5% or less by weight,
   wherein the probiotic bacterial preparation has a water activity of about 0.30 or less,
   wherein the hygiene tissue is a device for wiping skin of a user, the hygiene tissue being selected from the group consisting of a washcloth, towelette and wetwipe.

2. The hygiene tissue according to claim 1, wherein the composition comprises a liquid lipid phase.

3. The hygiene tissue according to claim 1, wherein the composition further comprises at least one additional component selected from the group consisting of water absorbent agents, tensides, pH buffering agents, perfume, antioxidants, and anti-inflammatory steroids.

4. The hygiene tissue according to claim 1, wherein the lactic acid producing bacterial strain is selected from the genera *Pediococcus, Lactococcus, Lactobacillus*, or mixtures thereof.

5. The hygiene tissue according to claim 1, wherein the lactic acid producing bacterial strain includes at least *Lactobacillus plantarum*.

6. The hygiene tissue according to claim 1, wherein the lactic acid producing bacterial strain includes at least *Lactobacillus plantarum* 931.

7. The hygiene tissue according to claim 1, wherein the lactic acid producing bacterial strain(s) is isolated from the skin or urogenital area of a healthy person.

8. The hygiene tissue according to claim 1, wherein the amount of lactic acid producing bacteria ranges from $10^4$-$10^{11}$ colony forming units (CFU) per tissue.

9. The hygiene tissue according to claim 8, wherein the amount of lactic acid producing bacteria ranges from $10^6$-$10^{11}$ colony forming units (CFU) per tissue.

10. The hygiene tissue according to claim 1, wherein the lipid is selected from the group consisting of canola oil, coconut oil, palm kernel oil, peanut oil, soy bean oil, Dimethicone, paraffin oil, and petrolatum.

11. The hygiene tissue according to claim 1, wherein the water activity is about 0.25 or less.

12. The hygiene tissue according to claim 1, wherein the water activity is about 0.20 or less.

13. The hygiene tissue according to claim 1, wherein the matrix of the hygiene tissue has a water content of 1% or less by weight.

14. The hygiene tissue according to claim 1, wherein the lipid phase has a water content of about 1% or less by weight.

15. The hygiene tissue according to claim 1, wherein the hygiene tissue is individually packed in a moisture impervious packing unit, wherein the moisture impervious packing unit has a water vapor transmission rate of 6 $g/m^2$/calendar day or less.

16. A method of cleaning and simultaneously establishing and maintaining a beneficial microbial flora on skin or urogenital area, the method comprising: contacting the hygiene tissue of claim 1, to skin or urogenital area, to deliver the composition to the skin or urogenital area.

17. The method according to claim 16, wherein the matrix of the hygiene tissue has a water content of 1% or less by weight.

\* \* \* \* \*